(12) United States Patent
Quinn

(10) Patent No.: US 7,108,674 B2
(45) Date of Patent: *Sep. 19, 2006

(54) CATHETER

(75) Inventor: David G. Quinn, Grays Lake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 630 days.

This patent is subject to a terminal disclaimer.

(21) Appl. No.: 10/265,805

(22) Filed: Oct. 7, 2002

(65) Prior Publication Data

US 2003/0032918 A1   Feb. 13, 2003

Related U.S. Application Data

(63) Continuation-in-part of application No. 09/853,511, filed on May 11, 2001, now Pat. No. 6,461,321, and a continuation-in-part of application No. 09/759,582, filed on Jan. 11, 2001, now Pat. No. 6,702,776, which is a continuation-in-part of application No. PCT/US00/32000, filed on Nov. 21, 2000, which is a continuation-in-part of application No. 09/651,763, filed on Aug. 30, 2000, now Pat. No. 6,517,529.

(60) Provisional application No. 60/266,617, filed on Feb. 6, 2001.

(51) Int. Cl.
    *A61M 3/00* (2006.01)

(52) U.S. Cl. .................. 604/43; 604/6.16; 604/266

(58) Field of Classification Search .............. 604/43, 604/2.16, 266, 270, 524, 523, 6.16; A61M 3/00
    See application file for complete search history.

(56) References Cited

U.S. PATENT DOCUMENTS

| | | |
|---|---|---|
| 1,879,249 A | 9/1932 | Honsaker |
| 2,116,083 A | 5/1938 | Rusch |
| 3,384,089 A | 5/1968 | Shriner |
| 3,589,368 A | 6/1971 | Jackson et al. |
| 4,037,599 A | 7/1977 | Raulerson |
| 4,134,402 A | 1/1979 | Mahurkar |
| 4,270,542 A | 6/1981 | Plumley |
| 4,311,140 A | 1/1982 | Bridgman |
| 4,368,737 A | 1/1983 | Ash |
| 4,381,011 A | 4/1983 | Somers, 3rd |
| 4,445,897 A | 5/1984 | Ekbladh et al. |
| 4,498,902 A | 2/1985 | Ash et al. |
| 4,529,399 A | 7/1985 | Groshong et al. |
| 4,549,879 A | 10/1985 | Groshong et al. |
| 4,559,039 A | 12/1985 | Ash et al. |
| 4,568,329 A | 2/1986 | Mahurkar |
| 4,583,968 A | 4/1986 | Mahurkar |

(Continued)

*Primary Examiner*—Kevin Sirmons
*Assistant Examiner*—Andrew Gilbert
(74) *Attorney, Agent, or Firm*—Brinks Hofer Gilson & Lione

(57) ABSTRACT

A catheter comprising a dual lumen tube with a bolus at its distal end having a bullet nose. A venous port is formed in one side of the bolus adjacent the bullet nose of the bolus. An arterial port is formed in the bolus circumferentially displaced 180° around the catheter from the venous port. The bolus contains a venous passage which transitions from a smaller two-thirds moon shaped cross-section to a larger circular cross-section. The arterial passage has a crescent-moon shaped cross-section. The bullet nose is not as thick as the tube and is inclined on an angle to the axis of the tube so that a portion of its outer periphery is substantially tangent to a hypothetical cylinder containing the trailing edge of the venous port.

46 Claims, 5 Drawing Sheets

U.S. PATENT DOCUMENTS

| | | |
|---|---|---|
| 4,623,327 A | 11/1986 | Mahurkar |
| 4,639,252 A | 1/1987 | Kelly et al. |
| 4,643,711 A * | 2/1987 | Bates .................. 604/6.16 |
| 4,671,796 A | 6/1987 | Groshong et al. |
| 4,692,141 A | 9/1987 | Mahurkar |
| 4,692,153 A | 9/1987 | Berlin et al. |
| 4,701,166 A | 10/1987 | Groshong et al. |
| 4,770,652 A | 9/1988 | Mahurkar |
| 4,772,266 A | 9/1988 | Groshong |
| 4,781,678 A | 11/1988 | de Couët et al. |
| 4,808,155 A | 2/1989 | Mahurkar |
| 4,842,582 A | 6/1989 | Mahurkar |
| 4,895,561 A | 1/1990 | Mahurkar |
| 4,898,669 A | 2/1990 | Tesio |
| 5,053,004 A | 10/1991 | Markel et al. |
| 5,197,951 A | 3/1993 | Mahurkar |
| 5,221,255 A | 6/1993 | Mahurkar et al. |
| 5,221,256 A * | 6/1993 | Mahurkar .................. 604/43 |
| 5,322,519 A | 6/1994 | Ash |
| 5,336,177 A | 8/1994 | Marcus |
| 5,374,245 A | 12/1994 | Mahurkar |
| 5,378,230 A | 1/1995 | Mahurkar |
| 5,451,216 A | 9/1995 | Quinn |
| 5,486,159 A | 1/1996 | Mahurkar |
| 5,571,093 A * | 11/1996 | Cruz et al. .................. 604/270 |
| 5,599,322 A | 2/1997 | Quinn |
| 5,607,405 A | 3/1997 | Decker et al. |
| 5,624,413 A | 4/1997 | Markel et al. |
| 5,685,836 A | 11/1997 | DiPerna et al. |
| 5,776,111 A | 7/1998 | Tesio |
| 5,947,953 A | 9/1999 | Ash et al. |
| 5,984,913 A | 11/1999 | Kritzinger et al. |
| 6,461,321 B1 * | 10/2002 | Quinn .................. 604/43 |

* cited by examiner

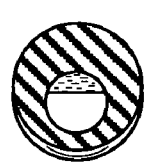
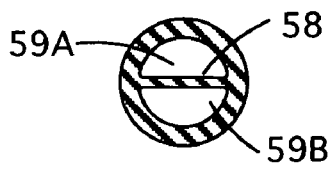
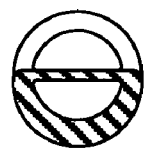
FIG. 6    FIG. 7    FIG. 8
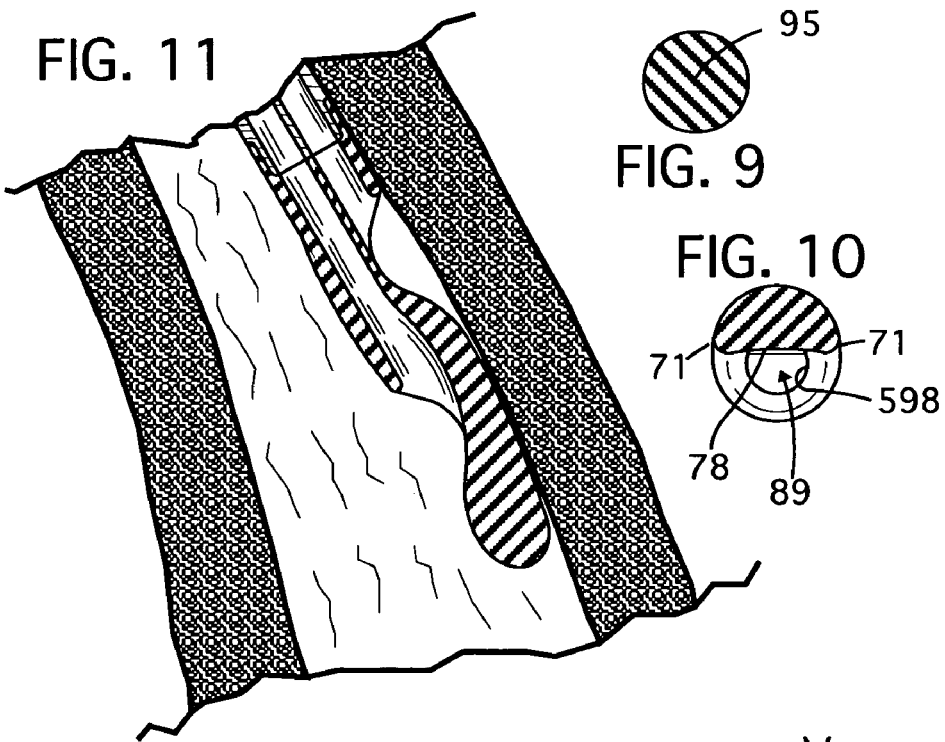
FIG. 11
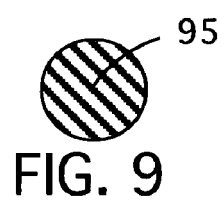
FIG. 9
FIG. 10
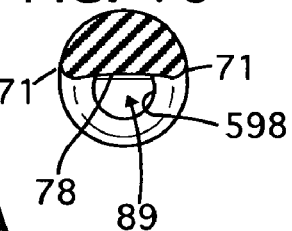
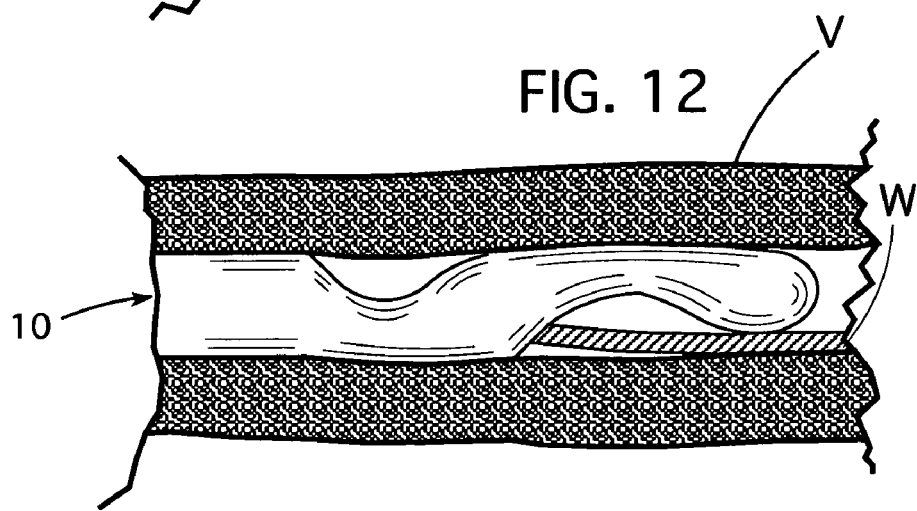
FIG. 12

0.192   0.038
         0.150

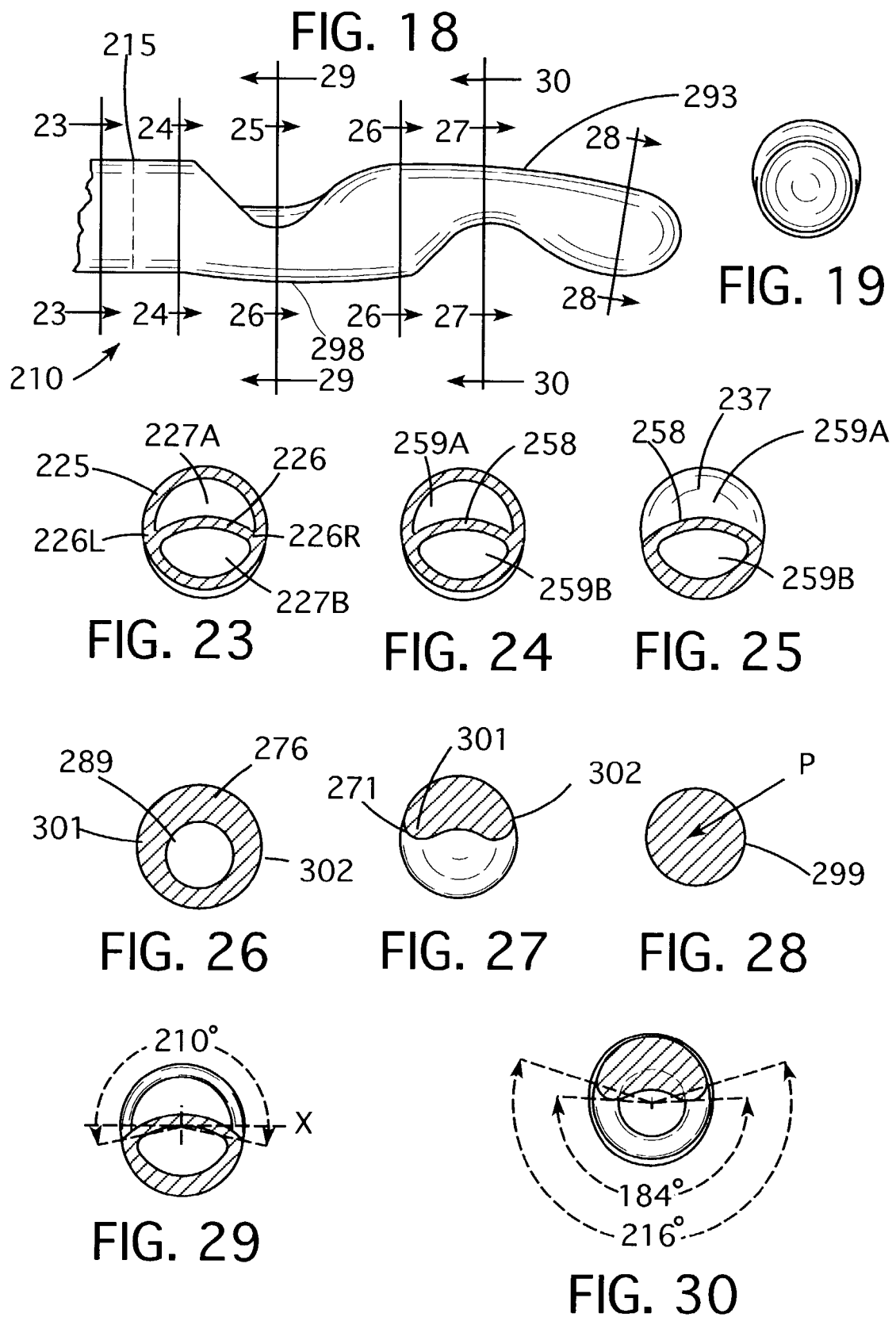

CATHETER

RELATED APPLICATIONS

This application is a continuation-in-part of U.S. application Ser. No. 09/853,511 filed May 11, 2001 now U.S. Pat. No. 6,461,321, which claims the benefit of provisional U.S. Application Ser. No. 60/266,617, filed Feb. 6, 2001. Application Ser. No. 09/853,511 is a continuation-in-part of U.S. application Ser. No. 09/759,582, filed Jan. 11, 2001 now U.S. Pat. No. 6,702,776, which is a continuation-in-part of PCT application Ser. No. PCT/US00/32000 designating the United States filed Nov. 21, 2000. PCT application Ser. No. PCT/US00/32000 designating the United States is, in turn, a continuation-in-part of U.S. application Ser. No. 09/651,763 filed Aug. 30, 2000 now U.S. Pat. No. 6,517,529.

FIELD OF THE INVENTION

This invention relates in general to catheters. It relates specifically to catheters for use in blood vessels. Hemodialysis catheters, employ the invention to particular advantage.

BACKGROUND OF THE INVENTION

Catheters are inserted in the vascular system of a patient for a variety of reasons. Hemodialysis and plasmaphoresis are two principal procedures using such catheters. Intravenous procedures of other types also employ them.

Hemodialysis, for example, normally employs one of two types of catheter to remove blood from the patient for processing and return processed blood to the patient. Most commonly, a catheter tube containing two lumens is used, each lumen having a generally semi-cylindrical or D-shape configuration. This type of catheter is frequently referred to as a dual lumen catheter. Alternatively, two tubes, each with a full cylindrical configuration, are used separately to remove blood for dialysis and return the processed blood.

Flow rates possible with conventional dual lumen catheters are usually lower than those achievable where separate tubes are used to remove blood from a vein for dialysis and then return processed blood back to the vein. Thus, the use of two tubes has become more and more popular as the capacity (maximum flow rate) of hemodialysis membranes has increased.

Hemodialysis membranes are now able to process blood at over 500 ml of flow per minute. Even higher processing rates are foreseeable. However, problems occur with both the line introducing purified blood back into the vein (the venous or outflow line) and the line removing blood for purification (the arterial or intake line) at flow rates above 300 ml per minute. A high flow rate from the venous line may cause whipping or "firehosing" of the tip in the vein with consequent damage to the vein lining. A corresponding high flow rate into the arterial line may cause the port to be sucked into the vein wall, resulting in occlusion. It should be understood, of course, that both lines normally access the superior vena cava and the designations are used for differentiation purposes.

Speed of flow through a catheter lumen, whether it be in a single lumen or a dual lumen catheter, is controlled by a number of factors including the smoothness of the wall surface, the internal diameter or cross-sectional area of the tube lumen, and the length of the tube lumen. The most important factor is the cross-sectional area of the tube lumen. The force or speed of the fluid flow in a tube lumen for a given cross-sectional area is controlled by the external pumping force, of course. This is a positive pressure pushing processed blood through the venous lumen and a negative (suction) pressure pulling unprocessed blood through the arterial lumen.

Problems encountered in providing for a high flow rate through a catheter are magnified in a dual lumen catheter construction. Because each of the lumens in a dual lumen catheter normally has a D-shape, it has been assumed that flow rates are limited. Furthermore, such dual lumen catheters are, to a great extent, catheters with a main port that opens at the end of a lumen substantially on the axis of the lumen. Thus, "firehosing" frequently results. Fire-hosing may damage the vein wall, triggering the build-up of fibrin on the catheter tip. Fibrin build-up may result in port occlusion.

There are dual lumen catheters which utilize side ports for both outflow and inflow. An example is the catheter disclosed in the Cruz et al. U.S. Pat. No. 5,571,093. However, such catheters have not been entirely successful in solving problems related to hemodialysis with dual lumen catheters, e.g., high incidences of catheter port occlusion as well as some degree of fire-hosing.

Catheters of almost all types are also pliable so that they do not damage body tissue when they are in-situ. Pliability can create a problem during insertion, however, because the catheters can kink when they meet resistance. Thus, there is often a need for a certain amount of stiffness so that the catheters can be directed within body vessels or cavities. There are currently two methods of providing this stiffness; stylets and guide wires.

A stylet can be a single or a twisted wire with a blunt end that is inserted into the catheter to make it stiff. The stylet is often used with bullet nose catheters and maintains its position within the catheter as the catheter is inserted. The stiffened catheter is advanced into the blood vessel with the stylet.

In contrast, guide wires are used to both stiffen the catheter and to provide a guide for the insertion. Commonly, the guide wire is inserted into the blood vessel before the catheter. The catheter is then inserted into the blood vessel over the wire, and follows the wire as it travels inside the vessel. Guide wires are most often utilized with catheters that are inserted deep into the body, such as with central venous catheters that are inserted into the heart. The thin guide wire more easily makes the bends and turns necessary for this type of placement.

In guide wire insertion where the catheter must be inserted over the guide wire, catheters with open ends are normally utilized to permit passage of the guide wire. These catheters are more likely to cause damage to body tissue during insertion than bullet nose catheters, for example, because of their flat ends and side edges. Open ended catheters are also more likely to damage tissue than bullet nose catheters while in-situ. Nevertheless, the need for deep catheter insertion has heretofore made guide wire insertion of open-ended catheters an accepted procedure in spite of the disadvantage of their flat or blunt end design.

As an alternative, bullet nose catheters have occasionally been used with guide wires in some applications by incorporating a small hole through the nose for the wire to pass through. This approach has generally been found undesirable, however, because the hole in the bullet nose can later collect particulate matter and be a focal point for infection.

SUMMARY OF THE INVENTION

An object of the invention is to provide an improved dual lumen catheter.

Another object is to provide a dual lumen, blood vessel catheter which accommodates flow rates substantially as high as the latest separate lumen catheters.

Still another object is to provide a dual lumen catheter which is capable of returning processed blood to the patient at high flow rates without harmful firehosing of the catheter tip.

Yet another object is to provide a dual lumen catheter which permits high flow rates while minimizing trauma and potential red cell damage so as to substantially avoid clotting.

A further object is to provide a dual lumen catheter which substantially reduces the incidence of port occlusion.

Still a further object is to provide a dual lumen catheter in which occlusion of the return line port is substantially avoided regardless of the flow rate.

Still a further object is to provide a dual lumen catheter for hemodialysis applications and the like which facilitates reversal of the venous and arterial lines to relieve port occlusion without increasing the potential for mixing of dialyzed blood with blood being removed for dialysis Another object is to provide an improved bullet nose bolus for use on blood vessel catheters ranging in size from 3 French to 22 French in any medical application.

A further object is to provide a bullet nose bolus that protects the leading edge of the catheter outflow or inflow port from rubbing against the blood vessel wall.

Another object is to provide a bullet nose bolus for a catheter that will not kink during insertion.

Another object is to provide an improved blood vessel catheter for use with a guide wire.

Another object is to provide a blood vessel catheter that does not collect particulate matter that can be a focal point for infection.

Still another object is to provide a bullet nose bolus for a catheter which is compatible with a guide wire yet does not require an axially extending hole for the guide wire through the nose of the bolus.

Another object is to provide a bullet nose bolus for a catheter that can be inserted easily with a guide wire through a flexible introducer sheath having essentially the same size as the catheter itself.

Another object is to provide a bullet nose bolus for a blood vessel catheter that follows a guide wire through bends in a patient's vein without causing increased resistance to passage through the vein.

Another object is to provide a bullet nose bolus that always presents a rounded surface to the vein wall, even when the catheter is following a guide wire around a bend in the vein.

Another object is to provide a bolus with a nose which is designed to flex away from the guide wire in only one direction.

The foregoing and other objects are realized in a first form of blood vessel catheter embodying the present invention by providing a dual lumen catheter including a bullet-nose bolus having a radially opening outflow or venous port and a radially opening intake or arterial port. The arterial port is circumferentially displaced 180° around the axis of the bolus from the venous port.

The venous port opens radially through the bolus immediately behind its bullet nose. A venous lumen in the catheter having a substantially D-shape cross-section communicates with a corresponding D-shape venous passage in the body of the bolus. That D-shape venous passage transitions into a circular cross-section venous passage before reaching the venous port, while increasing in cross-sectional area as it transitions from the substantially D-shape passage to the circular passage.

The arterial port is axially displaced from the venous port and opens radially through the bolus immediately behind the venous port, albeit 180° around the axis therefrom. The arterial port communicates directly with a corresponding D-shape arterial passage in the body of the bolus.

In front of the arterial port and opposite the venous port, the profile of the bolus curves in an arc toward the side of the bolus in which the venous port is disposed, creating a stiffening arch in the passage section opposite the venous port. From the trailing edge of the venous port forward, the passage section and the nose section are effectively inclined to the longitudinal axis of the bolus and tube, and toward the venous port side of the bolus. The bullet nose of the nose section is thus offset from the axis of the bolus toward the venous port.

The opposite side surfaces of the bolus, proceeding forward from the mid-point of the venous port, also taper inwardly in converging arcs toward the bullet nose section. Thus, the bolus nose section is both narrower in width and shorter in height, i.e., it is smaller in cross-section than the trailing remainder of the bolus and the catheter tube itself.

Where the passage section joins the nose section of the bolus, on a plane extending transversely through the bolus in front of the venous port, the nose section has a maximum thickness in the plane on a line passing through the bolus axis and the center of the venous port. The thickness of the nose section is 20% to 25% less than the diameter of the catheter tube itself. The plane is inclined forwardly away from the port at an angle corresponding to the angle of inclination of the curving passage section toward the bolus axis.

The nose section of the bolus, not being as thick as the rest of the bolus but displaced radially to the venous port side of the longitudinal axis of the bolus passage section and catheter tube, is in a position wherein a portion of its outermost periphery is tangent to an imaginary cylinder containing the outer surface of the bolus passage section at the trailing edge of the venous port. This offset nose configuration prevents the vein wall from wrapping around the trailing edge of the port and being abraded thereby.

The stiffening arch defined in the bolus opposite the venous port inhibits folding of the bolus at the venous port during insertion of the catheter. Immediately opposite the arterial port, another stiffening arch is also formed in the bolus. The arch extends along that side of the bolus from a point radially aligned with the trailing edge of the arterial port to the trailing edge of the venous port. This arch inhibits folding of the bolus around the arterial port.

The catheter embodying this first form of the invention, with its novel bolus, lends itself ideally to insertion in a patient's vein over a guide wire. When inserted through the vein the bullet nose section flexes radially outwardly in a plane passing through the bolus axis and both ports under the influence of the guide wire. Because the nose section has a smaller thickness in that plane than the rest of the bolus and the tube, however, it is not forced outside the imaginary cylinder of the catheter. This makes for ease of insertion.

In a second form of catheter embodying features of the invention, the catheter tube has a modified dual lumen configuration of conventional design. The septum in the catheter tube is bowed so that the lumens have different cross-sectional shapes. The arterial lumen has a crescent-moon shaped cross-section while the venous lumen has a complementary, two-thirds moon shaped cross-section. The arterial and venous passages in the bolus have corresponding cross-sectional configurations. The arterial port extends around 210° of the bolus body circumference, and is substantially larger than in the first form of the invention.

In the second form of bolus the venous port is also modified. The bolus is formed so that the venous passage adjacent this port not only enlarges to a circular cross-section form as it approaches the port but curves toward the bolus axis. This results in a reduction in exit flow velocity of venous blood. The bolus wall at the trailing edge of the venous port is relatively thicker as a consequence of this venous passage curvature and less likely to abrade.

BRIEF DESCRIPTION OF THE DRAWINGS

The invention, including its construction and method of operation, is illustrated more or less diagrammatically in the drawings in which:

FIG. 6 is a cross-sectional view taken along line 6—6 of FIG. 1;

FIG. 7 is a cross-sectional view taken along line 7—7 of FIG. 1;

FIG. 8 is a cross-sectional view taken along line 8—8 of FIG. 1;

FIG. 9 is a cross-sectional view taken along line 9—9 of FIG. 1;

FIG. 10 is a cross-sectional view taken along line 10—10 of FIG. 1;

FIG. 11 is a longitudinal sectional view through a patient's vein with a catheter in-situ in a typical operational position;

FIG. 12 is a longitudinal sectional view similar to FIG. 5 showing the catheter is a patient's vein which bolus nose section flexed upwardly by a guide wire;

FIG. 18 is a side elevational view of a portion of a catheter embodying features of a second form of the invention;

FIG. 19 is a front end view of the catheter bolus in the catheter of FIG. 18;

FIG. 23 is a cross-sectional view taken along the line 23—23 of FIG. 18;

FIG. 24 is a cross-sectional view taken along the line 24—24 of FIG. 18;

FIG. 25 is a cross-sectional view taken along the line 25—25 of FIG. 18;

FIG. 26 is a cross-sectional view taken along the line 26—26 of FIG. 18;

FIG. 27 is a cross-sectional view taken along the line 27—27 of FIG. 18;

FIG. 28 is a cross-sectional view taken along the line 28—28 of FIG. 18;

FIG. 29 is a cross-sectional view taken along line 29—29 of FIG. 18; and

FIG. 30 is a cross-sectional view taken along line 30—30 of FIG. 18.

DESCRIPTION OF THE PREFERRED EMBODIMENT

Figure 1:
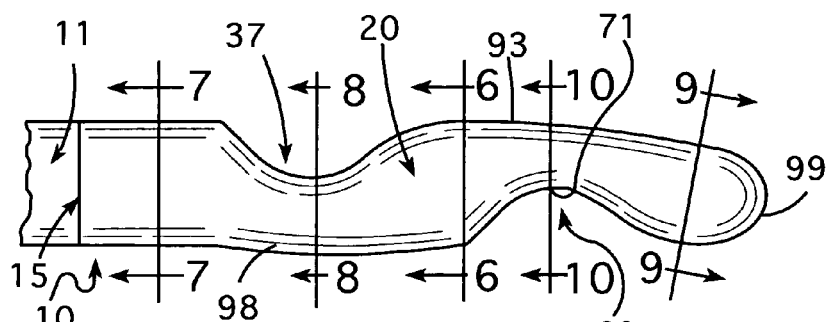
FIG. 1 is a side elevational view of a portion of a hemodialysis catheter embodying features of a first form of the invention.
Figure 2:
FIG. 2 is a front end view of the catheter bolus.
Figure 3:
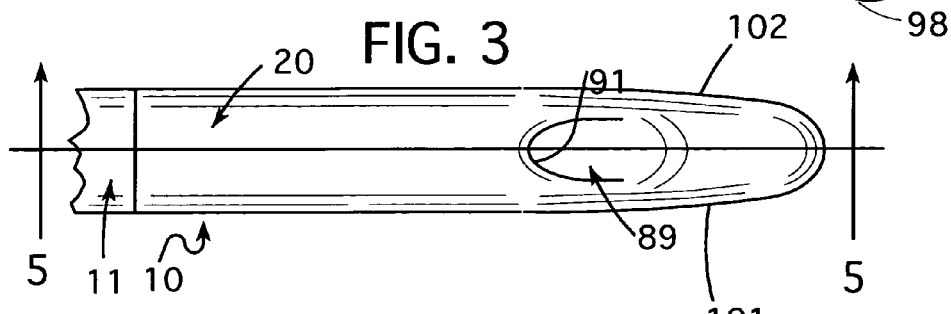
FIG. 3 is a bottom plan view of the bolus end of the catheter of FIG. 1.
Figure 4:
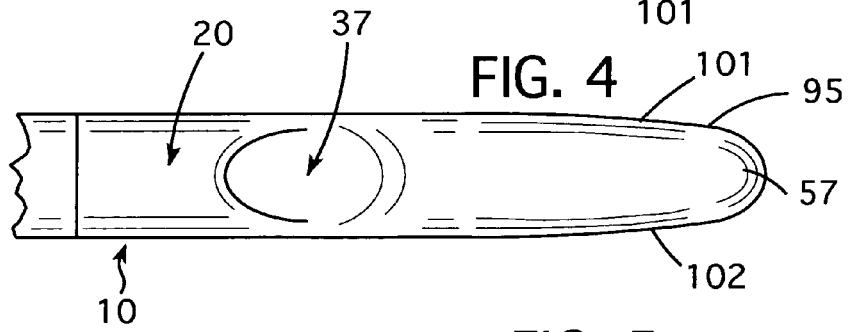
FIG. 4 is a top plan view of the bolus for the catheter of FIG. 1.
Figure 5:
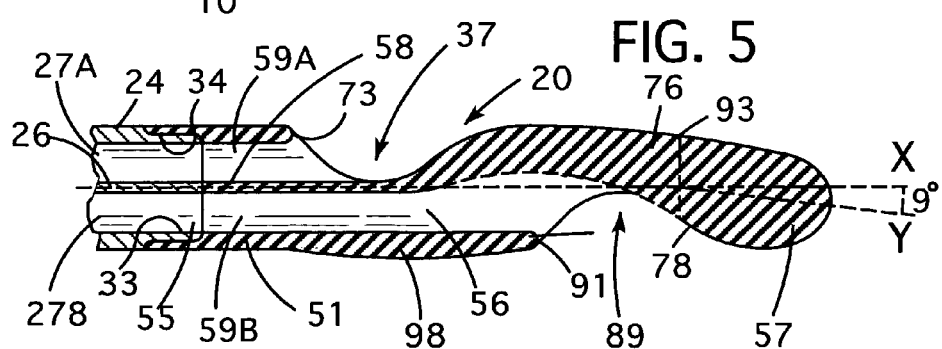
FIG. 5 is a longitudinal sectional view taken through the bolus of the catheter of FIG. 4.

Referring now to the drawings and particularly to FIGS. 1–10, a dual lumen catheter embodying features of a first form of the invention is illustrated generally at 10. The catheter 10 comprises a cylindrical tube 11 (only partially shown) having a distal end 15. A bolus 20 is attached to the distal end 15 of the tube 11.

The tube 11 illustrated is a standard 14.5 French tube formed of a plastic material such silicone or polyurethane. In this embodiment the tube 11 shown is formed of MED-4700 silicone and is manufactured by NuSil Technologies. The tube 11 is formed by extruding a tubular body 24 with a generally cylindrical wall 25 and a septum 26. The 14.5 French tube 11 has an O.D. of 0.192 inches.

The tube body 24 is divided by the septum 26 into two identical D-shape lumens 27A and 27B extending through the tube body along its length. The lumen 27A is normally an arterial lumen and the lumen 27B is normally a venous lumen. Each lumen 27A and 27B has a D-shape cross-sectional area of about 0.006 in$^2$ in a 14.5 French dual lumen tube.

The distal end 15 of the dual lumen tube body 24 has a necked down end 33 which is seated in a suitably formed socket 34 in the bolus 20. The bolus 20 has a body 51 also formed of silicone. The tube 11 and bolus 20 are mated in this relationship by conventional techniques.

The bolus body 51 includes a tube connector section 55, a flow passage section 56 and a nose section 57. The flow passage section 55 has a septum 58 formed in it. The septum 58 mates, end-to-end, with the septum 26 in the tube body 24.

The septum 58 forms upper and lower passages 59A and 59B in the flow passage section 56. The upper passage 59A is normally an arterial passage. The lower passage 59B is normally a venous passage.

The upper arterial passage 59A has a D-shape cross-section and extends forwardly with, and above, the septum 58 to the radial arterial port 37. Like the lumen 27A, the passage 59A has a cross-sectional area of about 0.006 in$^2$. The radial arterial port 37 extends circumferentially around the body's axis from the upper surface of the septum 58 on one side of the tube to the upper surface of the septum on its other side. The leading edge 73 of the bolus body 51 above the passage 59A, which forms the trailing edge of the port 37, is rounded along its length down to the septum 58 (see FIG. 4).

Forward of the arterial port 37 the bolus body 51 becomes solid, as at 76. In effect, the arterial passage 59A disappears and the septum 58 melds into this solid portion 76 of the bolus body 51.

Meanwhile, the venous passage 59B has a D-shape cross-section portion with a cross-sectional area of about 0.006 in$^2$ extending forwardly until the septum 58 ends. The venous passage 59B then gradually increases in size as it changes from a D-shape to a circular cross-section, as seen in FIG. 6. The circular cross-section of the passage 59B at the section line 6—6 has a cross-sectional area of about 0.007 in$^2$.

The cross-section of the passage 59B becomes fully circular (at section line 6—6) where it emerges over a base 78 which curves across the body 51 to form the front end of an axially elongated main outflow or venous port 89 in the body. The port 89 extends circumferentially around the body 51 to its side edges 71, as seen in FIG. 10. There it will be seen that the port 89 extends around approximately 230° of the circular cross-section passage 59B where it opens over the base 78 of the port. The port 89 has a trailing edge 91. The edge 91 is semi-circular in cross-section rounded along its length (see FIG. 5).

Where the port 89 begins, at its trailing edge 91, the outer surface of the solid portion 76 in the bolus body 51 opposite the port begins to curve inwardly to form a stiffening arch 93. The curve continues to where the arch 93 joins the nose section 57 at the base 95 of this section and then forwardly to the rounded bullet nose 99 on the nose section. The effective longitudinal axis Y of the passage section 57 forward of the trailing edge 91 of the port 89 is inclined to the longitudinal axis X of the trailing portion of the bolus body 51 at an angle of 9°. The arch 93 stiffens the bolus body 51 opposite the port 89 to prevent folding or kinking of the bolus 20 at that point as it travels through a vein during insertion.

Meanwhile, opposite the port 37 and behind the port 89, the bolus body is curved outwardly and then inwardly to form a stiffening arch 98. The arch 98 stiffens the bolus body 51 in the region of the port 37. The arch 98 serves to prevent folding or kinking of the bolus body 51 during insertion.

The side surfaces 101 and 102 of the bolus body 51, forward of the mid-point in the axially elongated port 89 and bracketing the arch 93, also curve inwardly to the nose section 57. This shape inhibits lateral flexing of the bolus nose section 57 during insertion.

The nose section 57 has a slightly elliptical shape in cross-section on the inclined plane P where it meets the nose section (see FIG. 9). The plane P is inclined forwardly relative to the axis X at an angle of about 81°. On the plane P, the nose section 57 is smaller in both width and thickness than the 14.5 French tube 11. In its preferred form, it is only about 10 French in size at this point and has a thickness of 0.150 inches which is 22% less than the diameter of the tube 11. In addition, the center of the nose section 57 on the axis Y is offset from the center of the bolus body 51 in the direction of the port 89.

The aforedescribed size, shape and orientation of the nose section 57 in the bolus body 51 provide several important advantages in use of the catheter 10. First, its smaller size facilitates easy entry of the bolus 20 into, and travel through, a patient's vein. Second, the offset nose section 57 places a portion of its periphery tangent to a hypothetical cylinder in which the outer surface of the bolus passage section 56 lies, even though it is considerably thinner than the remainder of the bolus. This prevents the vein wall from wrapping inwardly about the edge 91 of the port 89 and the edge then abrading the vein wall. Third, when guide wire insertion is employed, the nose section 57 flexes radially away from the wire where it emerges from the port 89, without forcing either the nose section or the wire substantially outside the aforementioned cylinder into the vein wall. Fourth, when traveling around curves in a vein during insertion, the bolus nose resists bending sideways and catching on the vein wall.

In regard to the second advantage referred to, attention is invited to FIG. 11 which shows the catheter 10 in a typical position in a vein V. There it will be seen that the periphery of the nose section 57 engages a vein wall when the passage section 56 does. This prevents the trailing edge 91 of the port 89 from having the vein wall wrap on it and become abraded.

During insertion, as seen in FIG. 12, the guide wire W causes the nose section 57 to flex outwardly until its axis Y is substantially parallel to the axis X of the bolus. However, the nose section 57, having a smaller cross-section generally and a smaller thickness particularly, does not protrude measurably outside the aforementioned cylinder.

Figure 13:
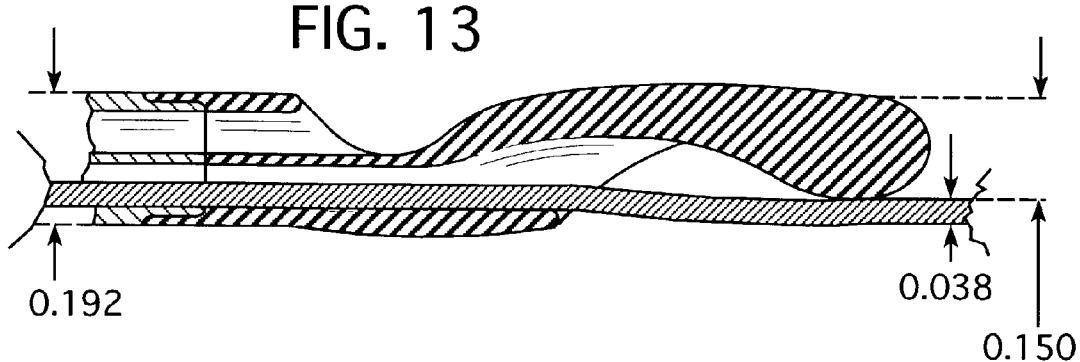
FIG. 13 is a longitudinal sectional view of a catheter being inserted over a guide wire (with the patient's vein not shown)

FIG. 13 shows the relative dimensions of the bolus 20 of the invention on a 10.5 French tube as it is inserted over a wire W, the inclined nose section 57 being flexed radially by the wire W but not outside the aforedescribed hypothetical cylinder. There it will be seen that the diameter of the tube 11 is 0.192 inches while the combined thickness of the wire W and nose section 57 is 0.188 inches.

Figure 14:
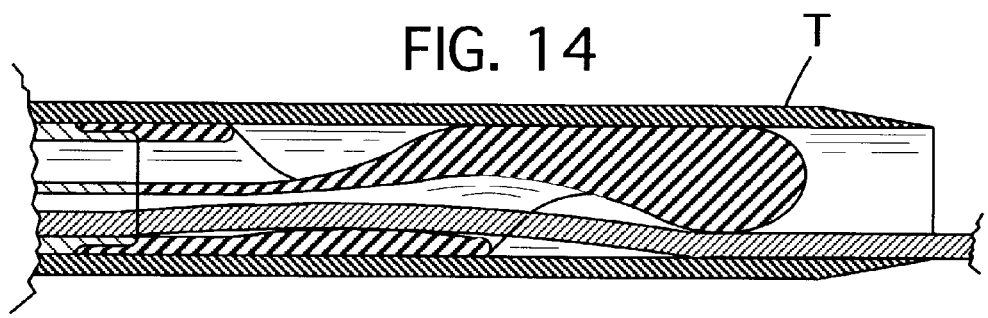
FIG. 14 is a longitudinal sectional view of a catheter prepared for introduction into a patient's vein over a guide wire and through an introducer tube.

As seen in FIG. 14, when the catheter 10 is inserted into an introducer tube T, the nose section 57 of the bolus 20 flexes upwardly to let the wire W pass. Because the nose section 57 has a smaller cross-section than the rest of the bolus body 51 and the tube 11, it is not compressed against the vein wall and frictional resistance to its passage is not measurably increased.

Figure 15:
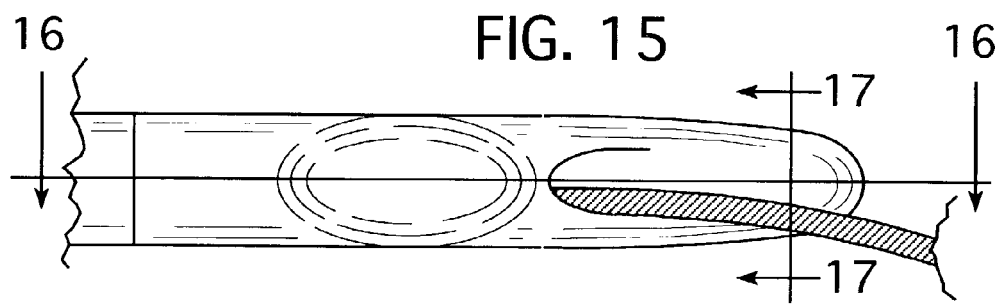
FIG. 15 is a bottom plan view of a catheter bolus and guide wire showing their relative orientation as the catheter is led around a turn in a patient's vein.
Figure 16:
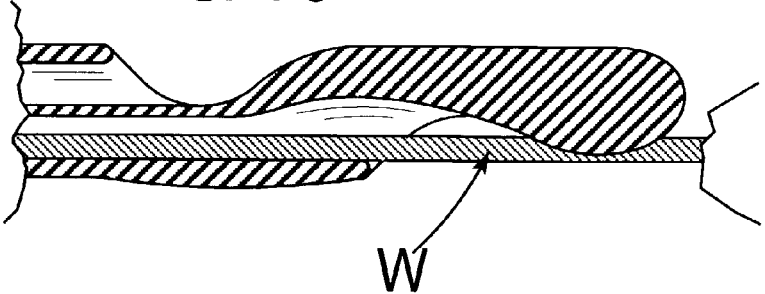
FIG. 16 is a longitudinal sectional view taken along line 16—16 of FIG. 15.
Figure 17:
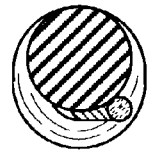
FIG. 17 is a cross-sectional view taken along line 17—17 of FIG. 15.
Figure 20:
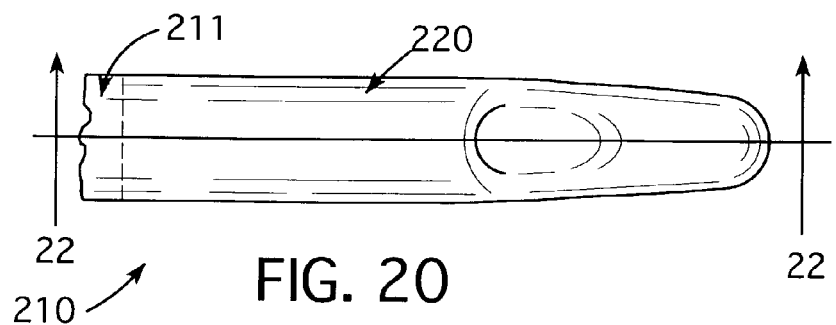
FIG. 20 is a bottom plan view of the bolus end of the catheter of FIG. 18.
Figure 21:
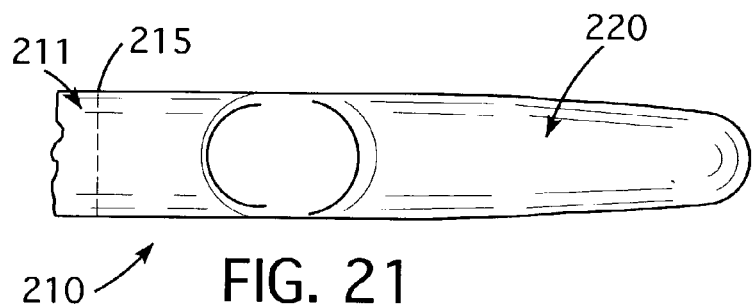
FIG. 21 is a top plan view of the bolus for the catheter of FIG. 18.

FIGS. 15–17 illustrate the catheter bolus 20 following the guide wire W around a turn in a vein (not shown). Here it will be seen that the wire W moves to one side of the nose section 57 and nestles alongside it. The bolus 57 sides curve inwardly from the mid-point of the port 89 forward, as has previously been pointed out. This shape tends to stiffen the bolus tip against lateral flexing.

With the catheter 10 in use in a patient, it has a number of important operational characteristics, some of which will be emphasized here. Because the lumen 59B in the bolus body 51 increases in size and becomes circular in cross-section as it approaches the venous bolus 89, pressure decreases, flow is more uniform and dialyzed blood is discharged through the venous port under less force. Should the arterial port 37 become clogged, the flow can be reversed to introduce dialyzed blood through port 37 and clear that port. Since the port 89 is relatively far removed from the port 37, dialyzed blood is not sucked directly into the port 89.

The present invention provides the physician with a bullet nose catheter 10 which can be inserted using a guide wire W but which does not require perforation of the bolus nose to facilitate passage of the guide wire. The nose section 57 of the bolus 20 flexes away from the bolus axis X to permit passage of the wire W but, in doing so, does not protrude measurably outside the imaginary cylinder defined by the rest of the bolus and the catheter tube, whereby the pressure of the bolus on vein V wall is not increased. Nevertheless, with the catheter 10 in operational position in a patient's vein V and the wire W removed, the nose section returns 57 to its normal position wherein it prevents the vein wall from wrapping around the bolus port edge 91 and becoming abraded thereby.

Referring now to FIGS. 18–30, a dual lumen catheter embodying features of a second form of the invention is illustrated generally at 210. The catheter 210 comprises a cylindrical tube 211 (only partially shown) having a bolus 220 is attached to its distal end 215. In the catheter 210 illustrated here, both the tube 211 and the bolus 220 are formed of polyurethane. Tecothane from Tecoflex, Inc. or Pellethane from Dow Chemical might be used, for example.

The tube 211 illustrated here is a 14 French tube. The tube 211 comprises a tubular body 224 with a generally cylindrical wall 225 and a septum 226. The 14 French tube 211 has an O.D. of 0.192 inches.

The tube body 224 is divided by the septum 226 into two lumens 227A and 227B extending through the tube body along its length. The lumen 227A is normally an arterial lumen and the lumen 227B is normally a venous lumen.

The tube 211 employed in this second form of the invention has a conventional "eyebrow" configuration of the type utilized in products of Arrow International, for example. In this regard, as best seen in FIG. 23 the cross-sectional shapes of its lumens 227A and 227B are complementary but not identical. The arterial lumen 227A has a crescent-moon shape. The venous lumen 227B has the shape of a two-thirds moon. These shapes are created by the fact that the septum 226 is bowed in cross-section in an "eyebrow" configuration between its left and right edges 226L and 226R, placing the edges well below the centerline of the tube 211. Nevertheless, the lumens 227A and 227B have virtually identical cross-sectional areas. For example, in the 14 French tube illustrated the cross-sectional area of the lumen 227A is 0.0073 in$^2$. While that of the lumen 227B is 0.0074 in$^2$.

The tube 211 and bolus 220 are separately formed of polyurethane. The distal end of the dual lumen tube body 224 may be formed with a necked down end which is seated in a suitably formed socket in the bolus 220 and mated in this relationship by sonic welding or the like. In the alternative, the tube 211 may simply have the bolus 220 joined by insert welding.

The bolus body 251, like the aforedescribed bolus body 51, includes a tube connector section 255, a flow passage section 256 and a nose section 257. The flow passage section 255 has a septum 258 formed in it. The septum 258 is welded, end-to-end, with the septum 226 in the tube body 224.

The septum 258 forms upper and lower passages 259A and 259B in the flow passage section 256. The upper passage 259A is normally an arterial passage. The lower passage 259B is normally a venous passage. As seen in FIG. 24, the upper arterial passage 259A has a crescent-moon cross-sectional shape identical to that of lumen 59A where it joins the tube body 224. The passage 259A extends forwardly with, and above, the septum 258 to the radial arterial port 237.

Figure 22:
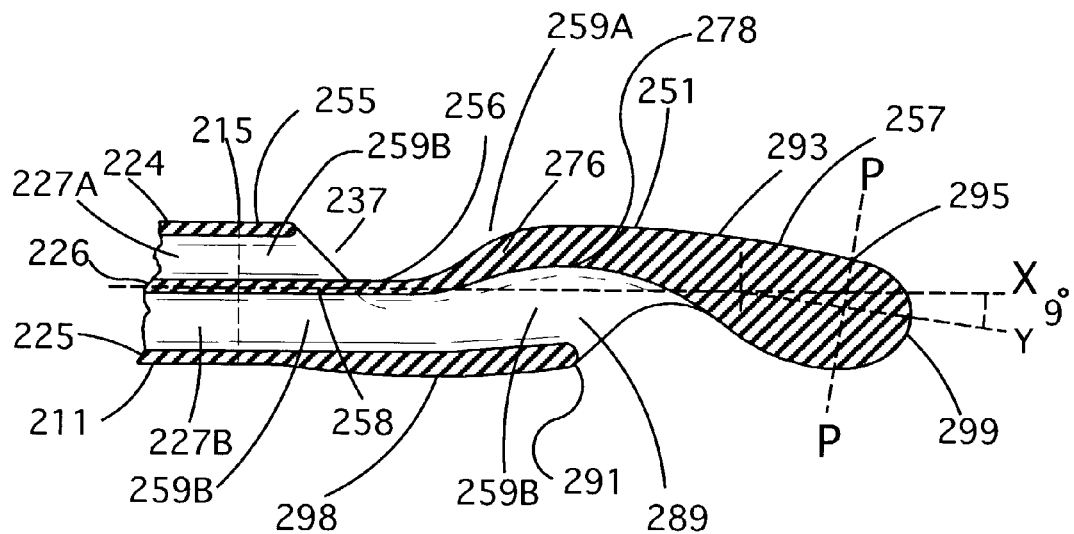
FIG. 22 is a longitudinal sectional view taken through the bolus of the catheter of FIG. 20.

The arterial port 237 extends circumferentially around the body's axis from the upper surface of the septum 258 on one side of the tube 211 to the upper surface of the septum on its other side, as seen in FIG. 22 and FIG. 25. The port 237 thus extends 210° around the periphery of the bolus body 251, creating a substantially larger port than the arterial port in the first form of the invention.

Forward of the arterial port 237, the bolus body 251 becomes solid, as at 276. The arterial passage 259A disappears. The septum 258 melds into the solid portion 276 of the bolus body 251.

Meanwhile, as also seen in FIG. 25, the venous passage 259B has a two-thirds moon shape cross-section extending forwardly until the septum 258 ends. The venous passage 259B then gradually changes to a circular cross-section, as seen in FIG. 26. It also increases slightly in cross-sectional area.

The cross-section of the passage 259B becomes fully circular where it emerges over a base 278 which curves across the body 251 to form the front end of an axially elongated main outflow or venous port 289 in the body. The port 289 extends circumferentially around the body 251 to its side edges 271, as seen in FIG. 27. The port 289 extends around approximately 215° of the circular cross-section passage 259B where it opens over the base 278 of the port. The port 289 has a trailing edge 291.

Where the port 289 begins, at its trailing edge 291, the outer surface of the solid portion 276 in the bolus body 251 opposite the port begins to curve inwardly to form a stiffening arch 293. The curve continues to where the arch 293 joins the nose section 257 at the base 295 of this section and then forwardly to the rounded bullet nose 299 on the nose section. As a result, the effective longitudinal axis Y of the passage section 257 forward of the trailing edge 291 of the port 289 is inclined downwardly relative to the longitudinal axis X of the trailing portion of the bolus body 251 at an angle of 9°. The arch 293 stiffens the bolus body 251 opposite the port 289 to prevent folding or kinking of the bolus 220 at that point as it travels through a vein during insertion.

Meanwhile, opposite the port 237 and behind the port 289, the bolus body is curved outwardly and then inwardly to form a stiffening arch 298. The arch 298 stiffens the bolus body 251 in the region of the port 237. The arch 298 serves to prevent folding or kinking of the bolus body 251 during insertion. As seen in FIG. 22, the arch 298 is formed here so that the thickness of the tube wall remains uniform forwardly of the center of the arch, creating a radially inwardly inclined venous passage 259B adjacent the port 289. This decreases flow velocity at the venous (outflow) port 289.

The side surfaces 301 and 302 of the bolus body 251, forward of the mid-point in the axially elongated port 289 and bracketing the arch 293, also curve inwardly to the nose section 257. This shape inhibits lateral flexing of the bolus nose section 257 during insertion.

The nose section 257 has a circular shape in cross-section, on the inclined plane P where it meets the nose section (see FIG. 28). The plane P is inclined forwardly relative to the axis X at an angle of about 81° thereto. On the plane P, the nose section 257 is smaller in both width and thickness than the 14 French tube 211. In its preferred form, it is only about 10 French in size at this point and has a thickness of 0.150 inches, which is 22% less than the diameter of the tube 211. In addition, the center of the nose section 257 on the axis Y is offset from the center of the bolus body 251 in the direction of the port 289.

The catheter 210 embodying the second form of the invention may be utilized in the same manner described above with regard to the catheter 10. It provides the same advantages in installation, use and removal. It provides the additional advantage of a bolus feature wherein higher flow rates are accommodated with lower outlet force at the venous port.

The "eyebrow" tube configuration of the catheter 210 also addresses a problem inherent in straight D-shaped dual lumen catheters. In a normal "D" tube configuration that is utilized in a high flow situation such as hemodialysis, the venous or "pushing" lumen tends to deform the "D" mid-septum. This deformation increases the overall cross-sectional area of the venous lumen while decreasing the effective size of the arterial or "sucking" lumen. This "sucking" in the arterial lumen further adds to the deformation of the septum. The "eyebrow" tube configuration directly addresses this distortion problem by pre-distorting the tube lumens. The two lumens are designed to have the same cross-sectional areas thereby minimizing the effect of the "push"/"pull" of the two pump lines.

In a catheter utilizing a "D" configuration, the arterial line is always the control for flow. The dialysis pump is forcing the same flow rate through both lumens. Therefore, the pressure in the effectively smaller arterial line is always higher than the pressure in the venous line. Flow rates can only be increased to the point where the arterial pressure remains under 250 mm Hg. This level is often reached well below the desired 400–500 ml per min. flow rate. If the lines needed to be reversed, the "bridge" configuration of the septum resists the tendency to be "pushed" or distorted. However, if for some reason the flow into the arterial line (previously the venous line) becomes occluded or reduced, then the septum of the eyebrow can be pushed beyond the strength limits of its bridge shape and snap into the space of the new arterial line, thereby greatly reducing arterial flow.

The improved recessed port design of the second eyebrow form of the invention greatly reduces this potential for port occlusion if the lines need to be reversed. The eyebrow version of the invention provides the preferred configuration of the invention. Flow is improved over the normal "D" in the standard venous/arterial mode, and is maintained in the reversed mode.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

The invention claimed is:

1. A bolus for a blood vessel catheter, comprising:
  a) a generally cylindrical body molded of resilient plastic and including a rear connector section, a front nose section and an intermediate passage section arranged in axially aligned relationship;
  b) said intermediate passage section containing first and second axially extending passages having a septum therebetween, said first passage communicating with a first port opening radially out of said cylindrical body in said passage section, said second passage communicated with a second port opening radially out of said cylindrical body in said passage section;
  c) said septum being bowed in the direction of said first passage whereby said first passage has a substantially crescent-moon shape in cross-section;
  d) each of said ports having a trailing edge extending around a portion of the circumference of said bolus body;
  e) said front nose section having a rounded bullet nose;
  f) said second passage having one cross-sectional area adjacent said connector section and another cross-sectional area where it communicates with said second port, said other cross-sectional area being greater than said one cross-sectional area.

2. The bolus of claim 1 further characterized in that:
  a) said second passage where it communicates with said second port being inclined toward the axis of said bolus.

3. The bolus of claim 2 further characterized in that:
  a) said second passage has an outer passage wall in said second passage adjacent said second port.

4. The bolus of claim 1 further characterized in that:
  a) said front nose section begins at the front end of said second port and has a maximum thickness at that point which is less than the outside diameter of said passage section at said trailing edge of said second port.

5. The bolus of claim 4 further characterized in that:
  a) said bolus body includes an axially extending stiffening arch formed in its outer periphery opposite said second port.

6. The bolus of claim 4 further characterized in that:
  a) said bolus body includes an axially extending stiffening arch formed in its outer periphery opposite said first port.

7. The bolus of claim 1 further characterized in that:
  a) said nose section has a center which is offset to one side of the longitudinal axis of said bolus in the direction of said second port so that a portion of the outer periphery of said bullet nose section normally is substantially tangent to an imaginary cylinder containing the outer surface of said passage section.

8. The bolus of claim 1 further characterized in that:
  a) said nose section is circular in cross-sectional configuration where it joins said passage section.

9. The bolus of claim 1 further characterized in that:
  a) said bolus body has converging side walls from about the mid-point of said second port forwardly.

10. The bolus of claim 1 further characterized in that:
  a) first port extends around more than 180° of the circumference of said bolus body; and
  b) said second port extends around more than 180° of the circumference of said second passage where it communicates with said second port.

11. The bolus of claim 1 further characterized in that:
  a) said second port opens on a radial which is approximately 180° from the radial on which said first port opens.

12. A bolus for a hemodialysis catheter, comprising:
  a) a general cylindrical body molded of resilient plastic and including a rear connector section, a front nose section and an intermediate passage section arranged in axially aligned relationship;
  b) said intermediate passage section containing first and second axially extending passages having a septum therebetween bowed in the direction of said first passage, said first passage communicating with a first port opening radially out of said cylindrical body in said passage section, said second passage communicating with a second port opening radially out of said cylindrical body in said passage section;
  c) each of said ports having a trailing edge extending around more than 180° of the circumference of said bolus body;
  d) said front nose section having a maximum thickness which is less than the diameter of the trailing portion of the bolus and having a rounded bullet nose;
  e) said front nose section also having a longitudinal axis which is inclined to the longitudinal axis of said bolus in the direction of said second port so that a portion of the outer periphery of said bullet nose section is normally substantially tangent to an imaginary cylinder containing the outer surface of said passage section at said trailing edge of said second port even though its maximum thickness is less than the diameter of the trailing portion of the bolus.

13. The bolus of claim 12 further characterized in that:
a) said front nose section beginning at the front end of said second port and having a cross-section at that point which are less than the cross-sectional of said passage section.

14. The bolus of claim 12 further characterized in that:
a) said bolus body includes an axially extending stiffening arch formed in its outer periphery opposite said second port.

15. The bolus of claim 12 further characterized in that:
a) said bolus body includes an axially extending stiffening arch formed in its outer periphery opposite said first port.

16. The bolus of claim 12 further characterized in that:
a) said first passage has a substantially uniform cross-sectional area along substantially its entire length; and
b) said second passage has one cross-sectional area adjacent said connector section and another cross-sectional area where it communicates with said second port, said other cross-sectional area being greater than said one cross-sectional area.

17. The bolus of claim 12 further characterized in that:
a) said bullet nose section is circular in cross-sectional configuration where it joins said passage section.

18. The bolus of claim 12 further characterized in that:
a) said bolus body narrows in plan configuration from the mid-point of said second port forwardly.

19. The bolus of claim 12 further characterized in that:
a) said first port extends around more than 200° of the circumference of said bolus body
b) said second port extends around more than 200° of the circumference of said second passage.

20. The bolus of claim 12 further characterized in that:
a) each of said trailing edges is approximately semi-circular in cross-section along its entire length.

21. A blood vessel catheter comprising:
a) a tube containing a first lumen and a second lumen, said tube having a distal end through which said lumens open;
b) an axially elongated bolus having a connector section connected to said distal end of said tube, a passage section containing a first passage and a second passage, and a nose section;
c) said nose section having a rounded nose which is unperforated;
d) said passage section forming at least portions of a first radially extending port communicating with said first passage and a second radially extending port communicating with said second passage;
e) said nose section beginning immediately adjacent the front end of said second port and having a maximum thickness which is at least 20% less than the outside diameter of said tube;
g) said radially extending ports being displaced approximately 180° from each other around the circumference of said catheter.

22. The catheter of claim 21 further characterized in that:
a) said nose section of said bolus has a longitudinal axis which is inclined at an angle to one side of a longitudinal axis of said tube distal end in the direction of said second port so that said rounded nose is offset to that side of said tube distal end axis.

23. The bolus of claim 22 further characterized in that:
a) said bolus body has outer side walls which converge from about the mid-point of said second port, forwardly.

24. The catheter of claim 21 further characterized in that:
a) said nose section of said bolus has a longitudinal axis which is inclined at an angle to one side of a longitudinal axis of said tube distal end in the direction of said second port so that a portion of the outer periphery of said rounded nose is normally substantially tangent to an imaginary cylinder containing the outer surface of said tube distal end even though its maximum thickness is less than the outside diameter of said tube.

25. The catheter of claim 21 further characterized in that:
a) said bolus body has outer side surfaces which converge from the mid-point of said second port forwardly to the tip of said rounded nose.

26. The catheter of claim 22 further characterized in that:
a) said longitudinal axis of said nose section extends through the center of the tip of said rounded nose and is inclined from said longitudinal axis of said tube distal end at an acute angle.

27. The catheter of claim 26 further characterized in that:
a) said acute angle is about 9°.

28. A blood vessel catheter, comprising:
a) a catheter tube formed of resilient plastic, said tube having a distal end and containing a first lumen and a second lumen separated by a septum;
b) a bolus having a body molded of resilient plastic and including a rear connector section and a front nose section;
c) said connector section being fastened to said distal end of said tube;
d) said bolus forming a first port opening radially out of said catheter and communicating with said first lumen and a second port opening radially out of said catheter and communicating with said second lumen;
e) said nose section having a bullet nose beginning immediately at the front end of said second port and;
f) the thickness of said nose section at the front end of said second port being substantially less than the diameter of said catheter behind said second port.

29. The blood vessel catheter of claim 28 further characterized in that:
a) said nose section is offset to one side of the longitudinal axis of said bolus in the direction of said second port so that a portion of the outer periphery of said nose section normally is substantially tangent to an imaginary cylinder containing the outer surface of said catheter immediately behind said second port.

30. The blood vessel catheter of claim 29 further characterized in that:
a) said nose section is approximately elliptical in cross-section where it joins said passage section.

31. The blood vessel catheter of claim 28 further characterized in that:
a) said bolus has side surfaces which, approximately at the mid-point of said second port, begin converging forwardly toward the axis of said bolus.

32. A blood vessel catheter, comprising:
a) a catheter tube formed of resilient plastic, said tube having a distal end and containing a first lumen and a second lumen separated by a septum;

b) a bolus having a body molded of resilient plastic and including a rear connector section and a front nose section;

c) said connector section being fastened to said distal end of said tube;

d) said bolus forming a first port opening radially out of said catheter and communicating with said first lumen and a second port opening radially out of said catheter and communicating with said second lumen;

e) said front nose section having a maximum thickness which is less than the diameter of the trailing portion of the catheter and having a rounded bullet nose;

f) said front nose section also having a longitudinal axis which is inclined to the longitudinal axis of said catheter in the direction of said second port so that a portion of the outer periphery of said bullet nose section is normally substantially tangent to an imaginary cylinder containing the outer surface of said catheter behind said second port even though its maximum thickness is less than the diameter of said catheter behind said second port.

33. The blood vessel catheter of claim 32 further characterized in that:

a) said front nose section begins at the front end of said second port and has a cross-section at that point which is smaller than the cross-section of said catheter behind said second port.

34. The blood vessel catheter of claim 32 further characterized in that:

a) said bullet nose section is elliptical in cross-sectional configuration where it joins said passage section.

35. The blood vessel catheter of claim 32 further characterized in that:

a) said bolus body narrows in plan configuration from the mid-point of said second port forwardly.

36. A hemodialysis catheter including a dual lumen tube and a bolus on a distal end of said tube, said bolus comprising:

a) a bolus body molded of plastic in a generally cylindrical shape about a longitudinal axis, said bolus body forming at least a portion of a radially extending first port and a radially extending second port in said catheter;

b) said radially extending first and second ports being angularly displaced from each other around the axis of said catheter;

c) said bolus body including a nose section forming a rounded front end on said bolus, the center of said nose section being radially offset from the axis of the catheter itself in the angular direction of said second port.

37. The catheter of claim 36 further characterized in that:

a) said first and second ports are angularly displaced from each other around said catheter by about 180°.

38. A hemodialysis catheter including a dual lumen tube and a bolus on a distal end of said tube, said catheter comprising:

a) a tube body containing first and second lumens; and b) a bolus body molded of resilient plastic;

c) said bolus body being fastened to said distal end of said tube and forming a radially extending first port in the side of said catheter and a radially extending second port in the side of said catheter;

d) said radially extending first and second ports being angularly displaced from each other approximately 180° around the axis of said catheter;

e) said bolus body including a nose section forming a rounded front end on said bolus in front of said second port;

f) said rounded front end is, at its largest cross-section, substantially smaller in cross-section than the rest of said bolus body;

g) the longitudinal axis of said nose section being inclined to the longitudinal axis of the catheter at its distal end whereby said nose section is directly in front of said second port.

39. A blood vessel catheter, comprising:

a) a catheter tube formed of resilient plastic and having a distal end;

b) a bolus having a body molded of resilient plastic and including a rear connector section and a front nose section, said front nose section including a rounded nose;

c) said connector section being fastened to said distal end of said tube;

d) said bolus forming at least a portion of a first port opening radially out of said catheter and a second port opening radially out of said catheter on a radial displaced approximately 180° around said catheter from said first port;

e) a first passage extending through said catheter into communication with said first port;

f) a second passage extending through said catheter into communication with said second port;

g) said first passage having a substantially uniform cross-sectional area along its entire length;

h) said second passage having substantially the same cross-sectional area as said first passage along most of its length but a larger cross-sectional area adjacent the end where it opens into said second port.

40. The catheter of claim 39 further characterized in that:

a) said nose section of said bolus has a longitudinal axis which is inclined at an angle to one side of a longitudinal axis of said tube distal end in the direction of said second port so that a portion of the outer periphery of said rounded nose is normally substantially tangent to an imaginary cylinder containing the outer surface of said tube distal end even though its maximum thickness is less than the outside diameter of said tube.

41. The catheter of claim 39 further characterized in that:

a) said bolus body has outer side surfaces which converge from the mid-point of said second port forwardly to the tip of said rounded nose.

42. The catheter of claim 40 further characterized in that:

a) said longitudinal axis of said nose section extends through the center of the tip of said rounded nose and is inclined from said longitudinal axis of said tube distal end at an acute angle.

43. The catheter of claim 39 further characterized in that:

a) said first passage is generally D shaped in cross-section along its entire length and said second passage is generally D shaped in cross-section along most of its length but is generally elliptical in cross-section at its larger end.

44. A hemodialysis catheter, comprising:

a) a catheter tube having first and second lumens separated by a septum;

b) a general cylindrical bolus body molded of resilient plastic and including a rear connector section and a front nose section arranged in axially aligned relationship, said rear connector section being mounted on said catheter tube;

c) said bolus body forming at least a portion of a first port opening radially outwardly of said catheter and communicating with said first lumen and at least a portion of a second port opening radially outwardly of said catheter and communicating with said second lumen;

d) said front nose section having a rounded bullet nose;

e) said second lumen communicating with said second port through a portion of the lumen which has a cross-sectional area greater than the cross-sectional area of the rest of said lumen.

45. The hemodialysis catheter of claim 44 further characterized in that:

a) said nose section has a center axis which is offset to one side of the longitudinal axis of said catheter tube in the direction of said second port so that a portion of the outer periphery of said bullet nose section normally is substantially tangent to an imaginary cylinder containing the outer surface of said catheter tube.

46. The bolus of claim 44 further characterized in that:

a) first port extends around less than 180° of the circumference of said catheter tube; and b) said second port extends around more than 180° of the circumference of said catheter tube.

* * * * *

UNITED STATES PATENT AND TRADEMARK OFFICE
CERTIFICATE OF CORRECTION

PATENT NO.       : 7,108,674 B2                                    Page 1 of 1
APPLICATION NO.  : 10/265805
DATED            : September 19, 2006
INVENTOR(S)      : David G. Quinn It is certified that error appears in the above-identified patent and that said Letters Patent is hereby corrected as shown below:

<u>On the Title Page</u>

In column 1, item (75), delete "Grays Lake" and substitute --Grayslake-- in its place.

<u>In the Claims</u>

Column 13, in claim 19, line 3, after "said bolus body" insert --.-- (period).

Signed and Sealed this

Twenty-seventh Day of March, 2007

JON W. DUDAS
*Director of the United States Patent and Trademark Office*